United States Patent [19]

Pearce et al.

[11] Patent Number: 4,625,277

[45] Date of Patent: Nov. 25, 1986

[54] BLOOD PRESSURE MEASURING DEVICE HAVING ADAPTIVE CUFF DEFLATION RATE

[75] Inventors: Christopher Pearce, Redmond, Wash.; Michel A. Lynch, Gainesville; Richard K. Davis, Altamonte, both of Fla.

[73] Assignee: Physio-Control Corporation, Redmond, Wash.

[21] Appl. No.: 617,124

[22] Filed: Jun. 4, 1984

[51] Int. Cl.$^4$ .............................................. G06F 15/42
[52] U.S. Cl. .................................... 364/416; 128/680; 128/681; 128/682; 128/683
[58] Field of Search ................ 364/416; 128/680, 681, 128/682, 683

[56] References Cited

U.S. PATENT DOCUMENTS

| | | | |
|---|---|---|---|
| 3,508,537 | 4/1970 | Kahn et al. | 128/2.05 |
| 4,116,230 | 9/1978 | Gorelick | 128/682 |
| 4,313,445 | 2/1982 | Georgi | 128/682 |
| 4,349,034 | 9/1982 | Ramsey, III | 128/682 |
| 4,360,029 | 11/1982 | Ramsey, III | 128/682 |
| 4,378,807 | 4/1983 | Peterson et al. | 128/682 |
| 4,517,986 | 5/1985 | Bilgutay | 128/680 |

Primary Examiner—Jerry Smith
Assistant Examiner—Kim Thanh Bui
Attorney, Agent, or Firm—Christensen, O'Connor, Johnson & Kindness

[57] ABSTRACT

A device is disclosed for making blood pressure measurements using an inflatable cuff (12), wherein the cuff deflation rate is established based upon prior blood pressure measurements. The cuff is adapted for applying pressure to a patient adjacent a blood vessel. the device includes means (14, 16) for inflating and deflating the cuff, a sensor system (60) for providing sensor signals during cuff deflation that correspond to the cuff pressure and to the blood flow surges in the blood vessel, and a process controller (100). The process controller causes inflation of the cuff to a first pressure and subsequent deflation of the cuff from the first pressure to a lower second pressure at a preestablished deflation rate, the inflation and subsequent deflation of the cuff comprising one measurement cycle. The process controller also processes the sensor signals provided during a given measurement cycle in order to determine at least one blood pressure value indicative of the patient's blood pressure for that measurement cycle. The process controller includes parameter setting means for establishing the cuff deflation rate for a given measurement cycle based upon the blood pressure value determined during at least one previous measurement cycle. The parameter setting means may establish the deflation rate based upon both blood pressure and pulse rate values determined during previous measurement cycles. The deflation rate may be established so as to provide a predetermined number of blood flow surges between systolic and diastolic pressures in the given measurement cycle.

10 Claims, 5 Drawing Figures

BLOOD PRESSURE MEASURING DEVICE HAVING ADAPTIVE CUFF DEFLATION RATE

FIELD OF THE INVENTION

The present invention relates to a noninvasive device for measuring blood pressure and, in particular, to an automatic blood pressure measuring device that includes an inflatable cuff.

BACKGROUND OF THE INVENTION

A well-known noninvasive technique for measuring a patient's blood pressure includes the steps of placing a cuff about the patient's limb, inflating the cuff to a pressure high enough to occlude an underlying blood vessel, and then deflating the cuff to a pressure lower than the patient's diastolic pressure. Measurements taken while the cuff pressure decreases are analyzed to determine the patient's pressure. In the oscillometric blood pressure technique, the measurements taken during cuff deflation include the total cuff pressure and the much smaller pressure fluctuations caused by blood flow surges in the underlying blood vessel. In the ausculcatory technique, the measurements taken include the total cuff pressure and the Korotkoff sounds corresponding to the blood flow surges. A third known technique makes use of an ultrasonic transducer and doppler detection means to detect the blood flow surges.

In one well-known application of the oscillometric technique, the cuff is first inflated to a pressure above the patient's expected systolic pressure, and then slowly deflated over a pressure range inclusive of the patient's systolic and diastolic pressures. During cuff deflation, the total cuff pressure is measured by an appropriate transducer in pneumatic communication with the cuff, and the output signal from this transducer is processed to yield signals corresponding to the total cuff pressure and to the smaller pressure fluctuations caused by blood flow surges. The signal corresponding to the blood flow surges is processed to determine the times during cuff deflation at which the cuff pressure was equal to the patient's systolic and diastolic pressures. The cuff pressures at such times are then displayed or otherwise output as the patient's blood pressure values. Analogous methods are known that make use of ausculcatory or ultrasonic techniques.

Circumstances frequently arise in which it is desirable to periodically monitor a patient's blood pressure over a period of time. Automatic blood pressure devices have therefore been produced that can make blood pressure measurements at a selected frequency (e.g., every five minutes) without operator intervention. The cuff deflation rate of an automatic blood pressure device is an important parameter. If the deflation rate is too high, then the cuff will deflate from systolic to diastolic pressure too rapidly, and unreliable blood pressure values will be produced. If on the other hand the deflation rate is too low, the cuff pressure will remain between systolic and diastolic pressures for an excessive period of time, resulting in patient discomfort.

Prior blood pressure measurement devices have either employed a preselected deflation rate, or have permitted operator selection between two or more rates. Devices using a single, preselected rate cannot be adjusted to suit individual patients. Devices permitting operator selection between two or more deflation rates can be matched to individual patient requirements for a single measurement. However in an automatic device, there is no guarantee that the selected deflation rate will remain suitable as the patient's blood pressure varies over time.

SUMMARY OF THE INVENTION

The present invention provides a blood pressure measuring device that automatically adapts its cuff deflation rate based upon blood pressure and pulse rate values determined during at least one previous measurement. The blood pressure measuring device of the present invention can therefore be used to periodically determine a patient's blood pressure without inaccuracy or patient discomfort.

In a preferred embodiment, the blood pressure measuring device of the present invention comprises an inflatable cuff, means for inflating and deflating the cuff, sensor means for providing sensor signals during cuff deflation corresponding to the cuff pressure and to the blood flow surges in an adjacent blood vessel, and process control means. The process control means comprises means for controlling the inflation and deflation means, calculation means, and parameter setting means. The inflation and deflation means are controlled such that the cuff is inflated to a pump-up pressure and subsequently deflated from the pump-up pressure to a lower hold-in pressure at a preestablished deflation rate. The inflation and subsequent deflation of the cuff comprise one measurement cycle. The calculation means processes the sensor signals provided during a given measurement cycle to determine at least one blood pressure value indicative of the patient's blood pressure for that measurement cycle. The parameter setting means establishes the deflation rate for a given measurement cycle based upon the blood pressure value determined during at least one previous measurement cycle.

In another aspect of the invention, the calculation means also processes the sensor signals provided during a given measurement cycle to determine a pulse rate value indicative of patient's pulse rate for that measurement cycle. The parameter setting means is operative to establish the deflation rate for a given measurement cycle based upon blood pressure and pulse rate values determined during at least one previous measurement cycle. The parameter setting means may be operative to establish a deflation rate selected such that if the patient's blood pressure remains constant, a predetermined number of blood flow surges will occur during the time in the given measurement cycle that the cuff is deflated from the patient's systolic pressure to the patient's diastolic pressure.

These and other features of the invention will become apparent in the detailed description and claims to follow, taken in conjunction with the accompanying drawings.

DETAILED DESCRIPTION OF THE INVENTION

Figure 1:
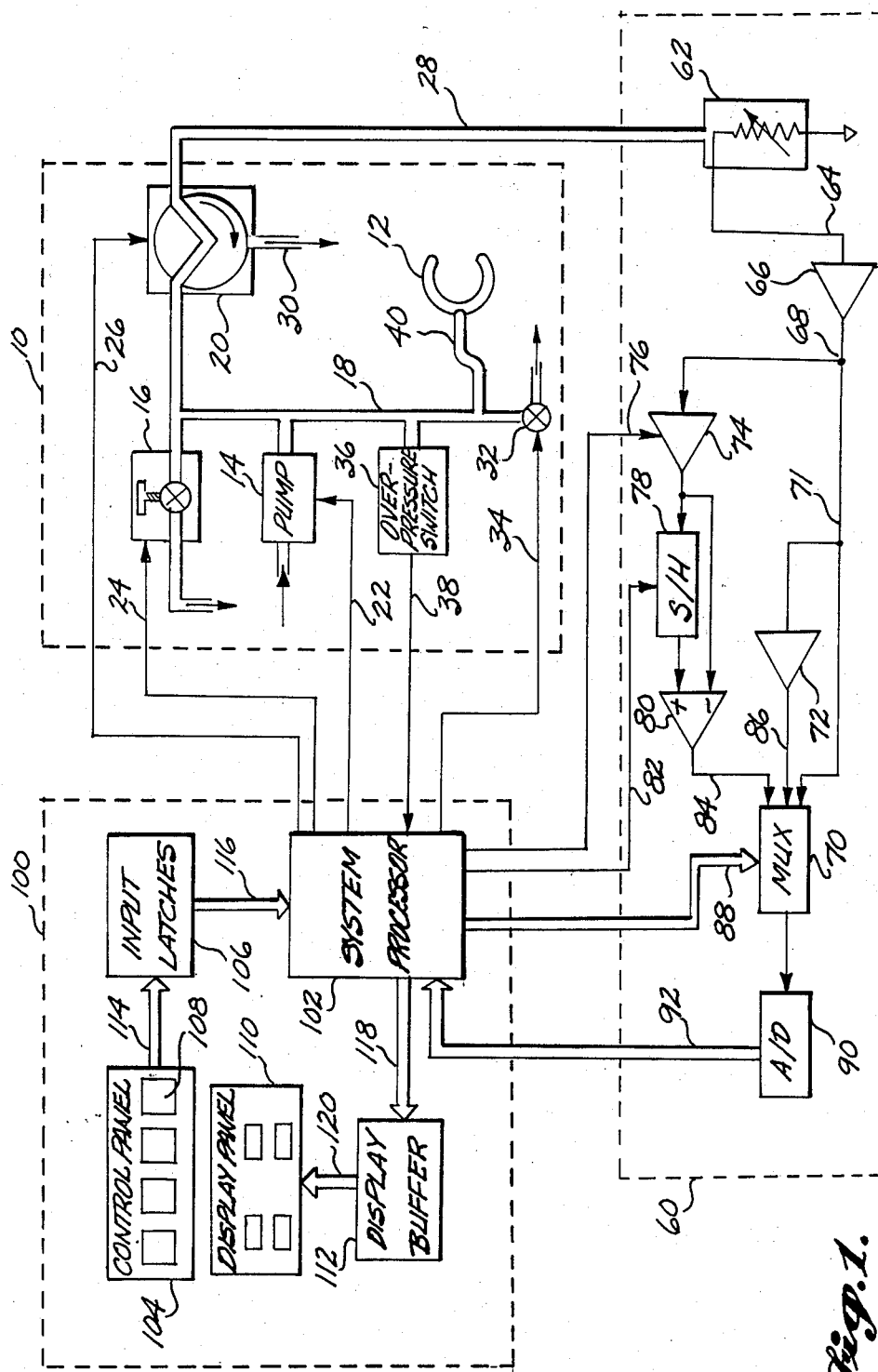
FIG. 1 is a block diagram of a blood pressure measuring device suitable for use in connection with the present invention.

Referring initially to FIG. 1, a blood pressure measuring device is shown that may be used for carrying out the present invention. The blood pressure measuring device comprises pneumatic system 10, sensor system 60, and process control system 100. Pneumatic system 10 includes cuff 12 that is adapted to be positioned adjacent a patient, e.g., around a patient's limb, such that the cuff is adjacent a blood vessel, i.e., and artery. The pneumatic system inflates and deflates the cuff in response to control signals provided by process control system 100. During cuff deflation, pressure sensor 62 of sensor system 60 produces a signal corresponding to the total pressure in the cuff. The sensor system extracts from that total pressure signal a separate signal corresponding to the pressure pulses caused by blood flow surges in the blood vessel, and provides the total pressure and pressure pulse signals in digital form to process control system 100. The process control system analyzes the digital signals, determines the patient's blood pressure and pulse rate, and displays the blood pressure and pulse rate values on display panel 110. When the device is in an automatic mode, the process control system also establishes the cuff deflation rate for the next measurement cycle based upon the blood pressure and pulse rate values determined during prior measurement cycles.

PNEUMATIC SYSTEM

Pneumatic system 10 includes cuff 12, pump 14, valve 16, manifold 18, and three-way valve 20. Cuff 12 is in pneumatic communication with pump 14, valve 16, and three-way valve 20 via tube 40 and manifold 18. In response to a signal on line 22 from the process control system, pump 14 inflates cuff 12 from the atmosphere. During inflation, valve 16 is closed and three-way valve 20 is in the position indicated in FIG. 1, such that pressure sensor 62 is in pneumatic communication with manifold 18. Process control system 100 is therefore capable of monitoring the pressure in cuff 12 via sensor system 60. When the process control system determines that the pressure in cuff 12 has reached a predetermined pump-up value, pump 14 is deactivated, and a signal is sent to valve 16 via line 24 to commence cuff deflation. During cuff deflation, the process control system monitors the signals provided by sensor system 60, and preferably controls the rate of air flow through valve 16 so as to produce a preestablished, linear deflation rate. Valve 16 may comprise any suitable valve capable of producing a variable air flow rate in response to an appropriate electrical signal. In one preferred embodiment, valve 16 comprises a needle valve controlled by a stepper motor.

The blood pressure measuring device shown in FIG. 1 includes a safety feature comprising overpresssure switch 36 and dump valve 32. Over pressure switch 36 monitors the pressure in manifold 18, and provides a corresponding signal to process control system 100 via line 38. If the process control system determines that the pressure in manifold 18 is too great, it activates dump valve 32 by means of a signal on line 34, and the dump valve responds by rapidly venting the pneumatic system to the atmosphere.

Three-way valve 20 is used to calibrate pressure sensor 62. At the outset of a blood pressure measurement, three-way valve 20 rotates in the direction indicated by the arrow such that passages 28 and 30 are interconnected, and are cut off from communication with manifold 18. Since passage 30 vents to the atmosphere, the pressure at pressure sensor 62 will then be equal to atmospheric pressure. Process control system 100 then records the (atmospheric) pressure signal provided by sensor system 60, and uses the recorded value to adjust subsequent cuff pressure readings.

SENSOR SYSTEM

Pressure sensor 62 may comprise a solid state strain gauge, or any other suitable pressure sensitive device. The pressure sensor produces a signal on line 64 which, except during calibration, bears a known relationship to the pressure within cuff 12. The signal on line 64 is amplified by amplifier 66, resulting in a signal at node 68 that corresponds to the total pressure in the cuff, including any pressure pulsations due to blood flow surges. Amplifier 66 may include a low pass filter to reject unwanted noise. The total pressure signal at node 68 is input to multiplexer 70 via line 71, and is also input to filters 72 and 74.

Filter 72 comprises a high-pass filter having a low cut off frequency of approximately 0.5 Hz. Filter 72 is therefore adapted to reject the slowly varying component of the total pressure signal node 68, and to pass the more rapidly varying pressure pulse signals caused by blood flow surges. The pressure pulse signal produced by filter 72 on line 86 thus represents the oscillometric pressure pulses that are analyzed by the process control system to determine the times during cuff deflation at which the cuff pressure is equal to the patient's systolic and diastolic pressures.

The total pressure signal at node 68 is also input into a servo circuit consisting of filter 74, sample and hold circuit 78 and differential amplifier 80. Filter 74 is a low-pass filter that preferably has a lower cut off frequency that can be varied between about 0.5 and 2.0 Hz in response to a signal from the process control system on line 76. The process control system may select the higher cut off frequency (2 Hz) whenever it detects comparatively rapid changes in the deflation rate. The output of filter 74 is input into sample and hold circuit 78 and into one input of differential amplifier 80. Sample and hold circuit 78 periodically samples the output of filter 74 in response to a trigger signal from the process control system over line 82, and provides the sampled value to the other input of differential amplifier 80. Thus as the output of filter 74 (i.e., the total cuff pressure) continues to vary after a sample has been taken by the sample and hold circuit, the inputs to differential amplifier 80 will slowly diverge from one another, and an increasing difference signal will be produced on line 84.

Multiplexer 70 sequentially samples the signals on lines 71, 86 and 84 in response to a channel select signal from process control system 100 via bus 88. Each sampled signal is digitized by analog-to-digital converter 90 and passed to the process control system via bus 92. The difference signal on line 84 is sampled at a preestablished time after triggering of the sample and hold circuit, and the resulting sampled difference signal therefore corresponds to the pressure decrease over a preestablished time, i.e., to the cuff deflation rate. The samples of the signals on lines 71 and 86 correspond to the total cuff pressure and the pressure pulsations, respectively.

PROCESS CONTROL SYSTEM

Process control system 100 comprises system processor 102, a control (input) system, and a display (output) system. The input system comprises control panel 104 and input latches 106. Control panel 104 includes a plurality of push button switches 108 that may be used by an operator of the device, as described below. Signals resulting from pushing a particular switch are passed to input latches 106 via bus 114, and subsequently from the input latches to the system processor via bus 116. The display system comprises display panel 110 and display buffer 112. Display panel 110 is preferably operative to display the patient's systolic pressure, diastolic pressure and pulse rate. Mean arterial pressure (MAP) may also be displayed. Signals representing the values to be displayed are passed via system processor 102 to display buffer 112 over bus 118, and are then conveyed to display panel 110 over bus 120.

Figure 2:
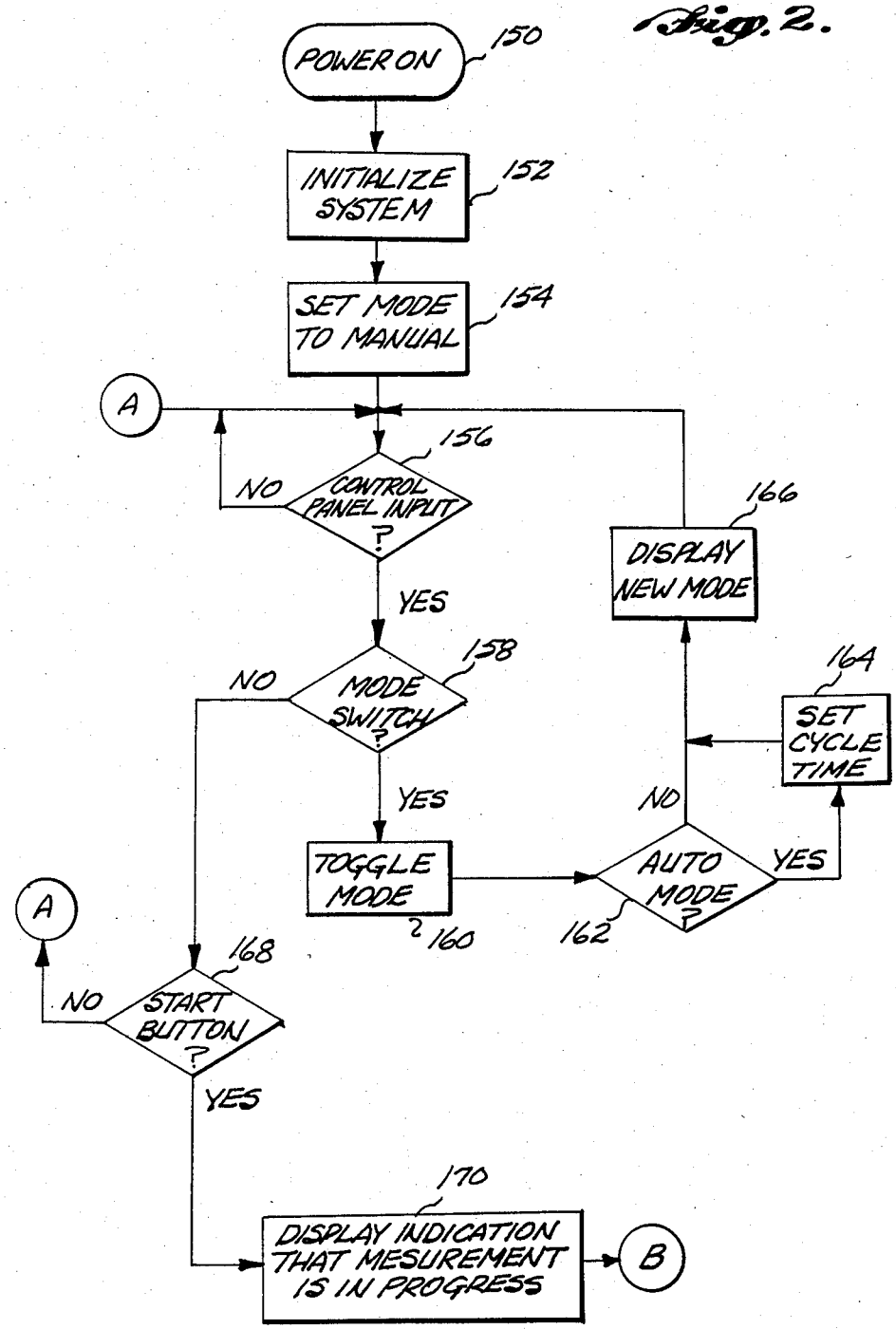
FIG. 2 is a flow chart of a portion of a program suitable for controlling operation of the device of FIG. 1.

FIGS. 2–5 set forth the flow chart of a program suitable for controlling the operation of system processor 102 in accordance with the present invention. Referring initially to FIGS. 1 and 2, program execution commences in block 150 when power is initially supplied to system processor 102 in response to an operator turning an on/off switch (not shown) to the "on" position. Block 152 then performs routine system initialization tasks, and block 154 sets a mode flag to manual. The program then waits in block 156 for operator input via control panel 104. Control panel 104 includes START, STOP, MODE and CYCLE TIME switches. When one of these switches is pushed, block 158 determines whether the switch pushed was the MODE switch. If the MODE switch was pushed, then block 160 toggles the mode flag, changing it to manual if it previously was automatic and to automatic if it previously was manual. Block 162 then checks to see if the mode flag is now set to automatic. If it is set to automatic, then block 164 prompts the operator to indicate the cycle time, i.e., the period of time that the device will wait before automatically repeating a blood pressure measurement. Any appropriate means may be used in block 164 for obtaining a cycle time value from the operator. In one preferred embodiment, block 164 causes display panel 110 to sequentially display a series of available cycle time values for as long as the operator holds the CYCLE TIME switch on control panel 104 depressed. The operator selects a particular cycle time by releasing the CYCLE TIME switch during the interval that the desired cycle time value is displayed. From block 162 or block 164, program flow passes to block 166, where the new mode and, if appropriate, cycle time is displayed. The program then returns to block 156 and awaits further input.

When block 158 determines that input from the control panel is not the MODE switch, then control passes to block 168, and block 168 determines whether the START switch has been pushed. If the START switch was not pushed, then control returns to block 156, and the device awaits further input. If the START switch has been pushed, then block 170 causes display panel 110 to indicate that a blood pressure measurement is in progress, and control passes to the measurement cycle routine shown in FIG. 3.

Figure 3:
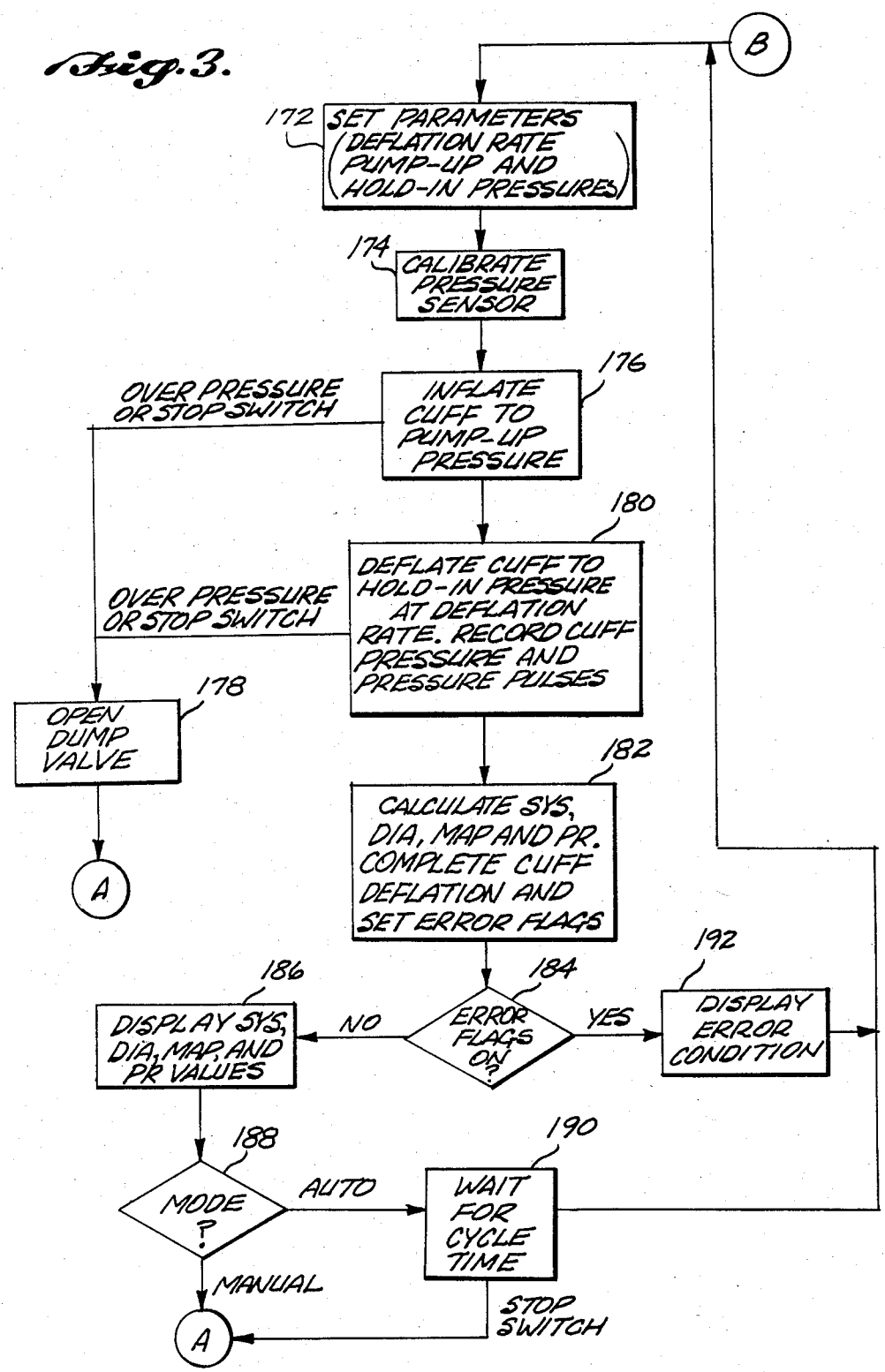
FIG. 3 is a flow chart of a portion of a program suitable for controlling operation of the device of FIG. 1.

Referring now to FIGS. 1 and 3, a measurement cycle commences at block 172 with the setting of three pneumatic system parameters: deflation rate, pump-up pressure and hold-in pressure. Details of the parameter setting routine are described below. Once these parameters have been set, the system processor executes a calibration step in block 174. The calibration step comprises activating three-way valve 20 such that atmospheric pressure is applied to pressure sensor 62, and then reading and storing the digitized value of the resulting total pressure signal. This digitized "zero" value therefore corresponds to atmospheric pressure, and is subtracted from all subsequently sampled total pressure values for the current measurement cycle. The digitized total pressure value is obtained by sending a channel select signal to multiplexer 70 over bus 88 that causes the multiplexer to select the signal on line 71 for input to analog-to-digital converter 90.

After calibration of the pressure sensor is complete, block 176 returns three-way valve 20 to the position indicated in FIG. 1, closes valve 16 and dump valve 32, and activates pump 14 to begin inflation of the cuff. As the cuff pressure increases, the total pressure signal provided by sensor system 60 is periodically monitored to determine whether the cuff pressure has reached the pump-up parameter set in block 172. During inflation, the system processor also periodically checks to see whether the STOP button on control panel 104 has been pushed, and whether the signal on line 38 from overpressure switch 36 indicates excessive cuff pressure. If either of these conditions is present, then control passes to block 178. Block 178 causes a signal to be produced on line 34 opening dump valve 32, thereby dumping the pressure in the cuff. Program control then returns to block 156 (FIG. 2), and the process control system awaits further input.

Assuming that the cuff inflates normally, block 176 passes control to block 180 when the pump-up pressure has been reached. Block 180 deactivates pump 14 and partially opens valve 16 to commence cuff deflation. During cuff deflation, system processor 102 varies the channel select signal on bus 88 so as to cause multiplexer 70 to cyclically sample the signals on lines 71, 86 and 84 for conversion by analog-to-digital converter 90. The total pressure samples (from line 71) and the pressure pulse samples (from line 86) are preferably stored, or preprocessed and stored for later analysis. Techniques for the processing of cuff pressure samples are well known to those skilled in the art. See for example U.S. Pat. No. 4,263,918. Each total pressure sample is also checked to see whether the cuff has deflated to the hold-in pressure. The difference sample (from line 84) is checked to see whether it corresponds to the value of the deflation rate parameter set in block 172. If the difference sample indicates that the deflation rate is too high or too low, then system processor 102 sends an appropriate signal to valve 16 over line 24 to modify the deflation rate. During deflation, the system processor in block 180 also periodically checks to see whether the STOP switch on control panel 104 has been pushed, and whether the signal on line 38 from overpressure switch 36 indicates excessive cuff pressure. If either of these conditions is present, then block 178 causes dump valve 32 to open, thereby dumping the pressure in the cuff, and program control returns to block 156 (FIG. 2).

When the program in block 180 determines that the cuff pressure has decreased to the hold-in pressure, then control passes to block 182. Block 182 causes the cuff deflation to continue, and simultaneously analyzes the recorded total pressure and pressure pulse samples to determine the systolic pressure (SYS), the diastolic pressure (DIA), and the pulse rate (PR). The mean arterial pressure (MAP) is preferably also determined. Any one of a number of well-known techniques may be used for performing such calculations. In general, such techniques involve analysis of the pressure pulse samples to determine the times during cuff deflation at which the cuff pressure was equal to the patient's systolic pressure, diastolic pressure, and mean arterial pressure. Once such times are known, the recorded values for total pressure at such times are taken to be the corresponding blood pressure values. The pulse rate may also be determined from the pressure pulse samples by any one of a number of well-known techniques. Any error encountered during the determination of the blood pressure or pulse rate values results in the setting of a corresponding error flag. The error flags are discussed in greater detail below. Block 182 preferably continues cuff deflation until the calculation of the blood pressure and pulse rate values (or the setting of error flags) is complete, or until the cuff pressure is equal to or less than about 15 mm, at which point dump valve 32 is opened to completely release the cuff pressure.

After the steps in block 182 have been completed, block 184 determines whether any error flags have been set. If block 184 determines that an error has occurred, then block 192 causes an appropriate display on display panel 110, and then returns control to block 172 to commence a new measurement cycle. If no errors have occurred, then block 186 displays the calculated values of systolic pressure, diastolic pressure, mean arterial pressure and pulse rate. Block 188 then determines whether the mode flag is set to manual or automatic. If manual mode is indicated, then control returns to block 156 (FIG. 2), and the system awaits further input. If the mode is automatic, however, then block 190 causes the system processor to wait for a period equal to the previously selected cycle time. If the STOP switch is pressed while the system processor is waiting in block 190, then control returns immediately to block 156. Assuming that the STOP switch is not pressed, then control returns to block 172 when the cycle time period expires, and the next measurement cycle is commenced.

Figure 4:
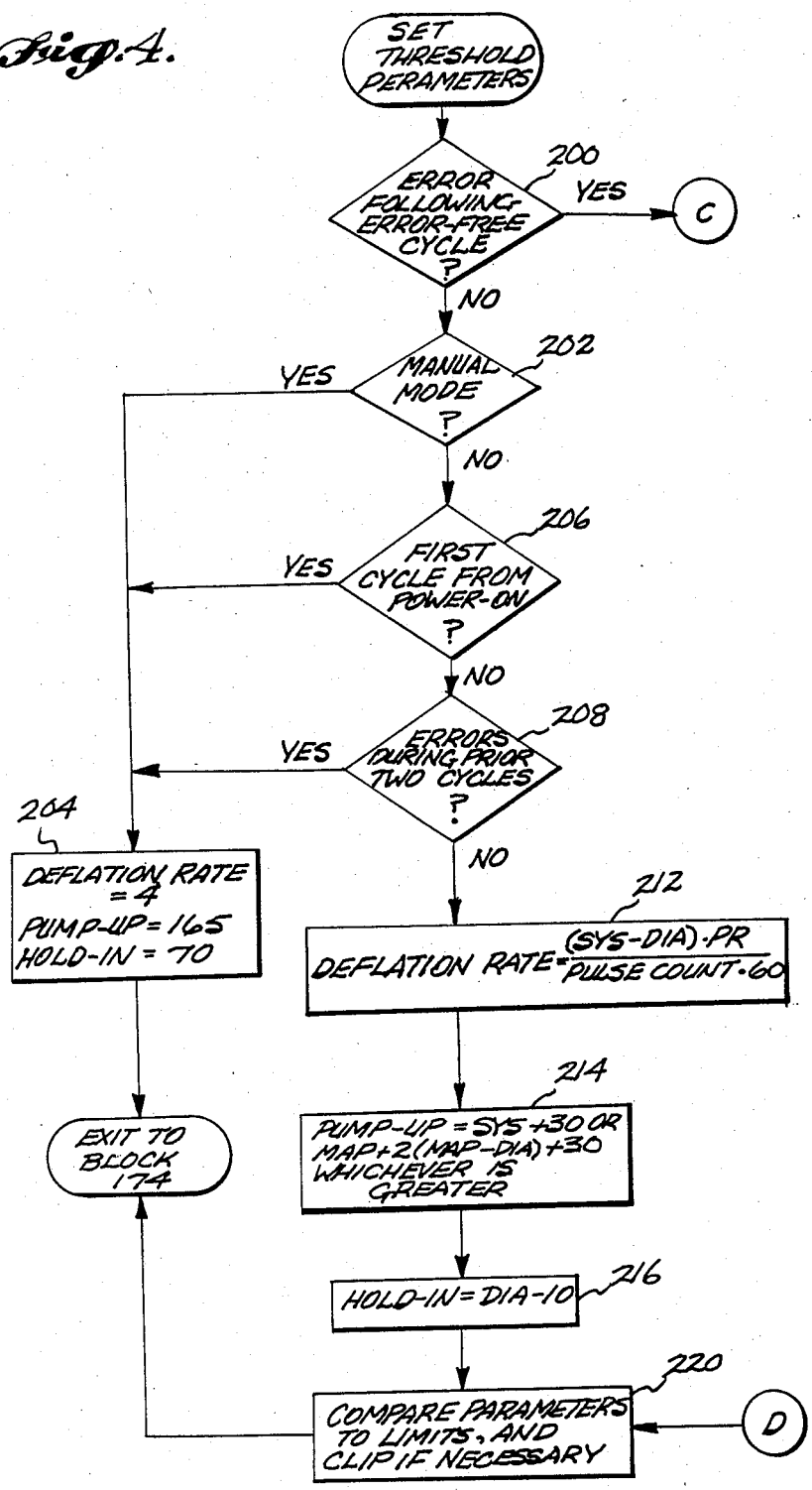
FIG. 4 is a flow chart of a portion of one preferred embodiment of the parameter setting portion of the program of FIG. 3.
Figure 5:
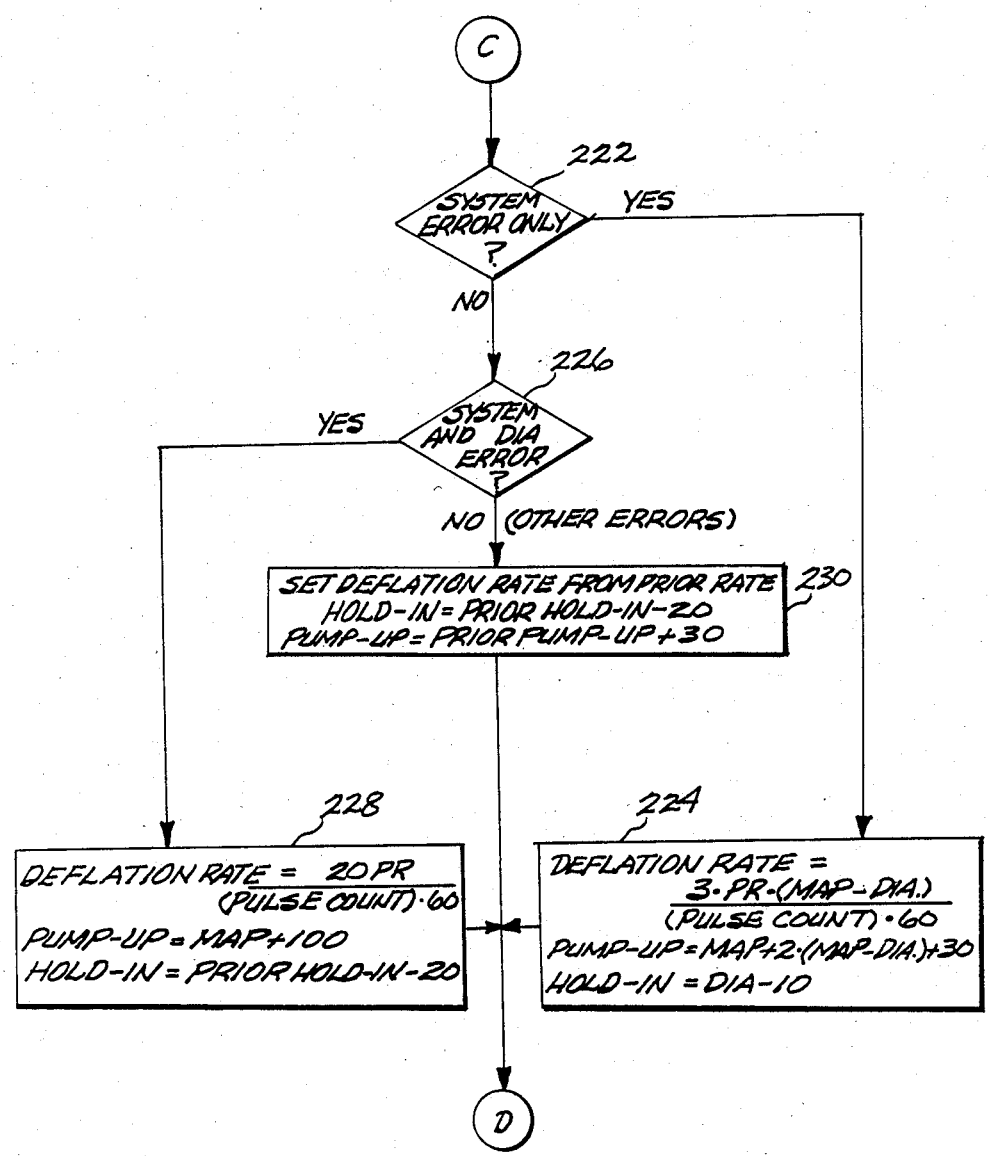
FIG. 5 is a flow chart of a portion of one preferred embodiment of the parameter setting portion of the program of FIG. 3.

FIGS. 4 and 5 correspond to block 172 of FIG. 3, and set forth one preferred embodiment of the method for setting the deflation rate, pump-up and hold-in parameters. The parameter setting sequence commences in block 200 which checks to see whether there has been an error during the immediately preceding measurement cycle (the "preceding" measurement cycle) following an error-free pass on the prior measurement cycle (the "second to last" measurement cycle). The test indicated in block 200 is performed regardless of whether or not the blood pressure device is in manual or automatic mode. If the test in block 200 is satisfied, then control passes to the error adaption routine of FIG. 5. If the test in block 200 is not satisfied, then block 202 checks to see whether the mode flag is set to manual. If manual mode is indicated, then block 204 sets the deflation rate equal to 4 mm/seconds, sets the pump-up pressure to 165 mm, and sets the hold-in pressure to 70 mm. These parameter values represent default values that are used during all cycles in manual mode except immediately after an error. Once the default values have been set, program control returns to block 174 of FIG. 3.

If the mode flag is set to automatic, then block 202 passes control to block 206. Block 206 determines whether the present cycle is the first cycle to be executed after the power was turned on. If so, then the default values of block 204 are used. If the present cycle is not the first cycle after power-on, then block 208 checks to see whether there have been two consecutive cycles with errors. If two consecutive error cycles have occurred, then the default parameters are used. If the test of block 208 is not satisfied, then the program performs the normal (error free) parameter adaption steps commencing at block 212.

Block 212 determines the deflation rate parameter by multiplying the difference between the systolic and diastolic pressures by the pulse rate, and dividing the product by the quantity PULSE COUNT times 60. The systolic, diastolic and pulse rate values used are those determined during the preceding measurement cycle. PULSE COUNT represents the number of pressure pulsations that should ideally occur in the time interval between the systolic and diastolic pressures. PULSE COUNT will therefore depend upon the particular blood pressure measurement technique, and on the particular algorithms used to calculate blood pressure from the blood flow surge data. For the oscillometric device illustrated in FIG. 1, preferred values for PULSE COUNT are preferably in the range of 10–12, with a PULSE COUNT value of 11 being optimum. Because the pulse rate is expressed as pulses per minute, the number 60 is provided in the denominator of the expression in block 212 so that the deflation rate will be expressed as a pressure change per second rather than per minute.

Block 214 sets the pump-up pressure for the current cycle equal to 30 mm plus the systolic pressure measured for the preceding measurement cycle. Preferably, the program also calculates the value:

$$MAP+2(MAP-DIA)+30 \qquad (1)$$

and sets the pump-up pressure to this latter value if it is greater than 30 plus the systolic pressure. Since for a normal individual:

$$MAP=(SYS+2DIA)/3 \qquad (2)$$

the two values calculated and compared in block 214 are usually about equal.

Block 216 calculates the hold-in pressure for the current measurement cycle by subtracting 10 mm from the diastolic pressure measured during the preceding measurement cycle. Block 220 then compares the deflation rate, pump-up and hold-in parameters to preselected limits and, if necessary, clips the parameter values such that they fall within the ranges defined by such limits. A preferred limiting range for deflation rate is 2–9 mm/second. A preferred limiting range for the pump-up pressure is 100–300 mm, and a preferred limiting range for the hold-in pressure is 30–90 mm. After the clipping in block 220 is complete, program execution returns to block 174 in FIG. 3.

FIG. 5 sets forth the steps used to set the deflation rate, pump-up and hold-in parameters after a measurement cycle in which an error occurred, assuming that the (preceding) measurement cycle in which an error occurred followed a (second to last) measurement cycle that was error free. Block 222 determines whether the error in the preceding measurement cycle related only to the calculation of the systolic pressure. If so, then the pneumatic parameters are calculated as indicated in block 224. As in FIG. 4, the blood pressure and pulse rate values used for parameter calculation in FIG. 5 are those obtained during the preceding measurement cycle. The deflation rate for the current measurement cycle is set equal to three times the pulse rate times the difference between the mean arterial pressure and the diastolic pressure, divided by 60 times the pulse count. This deflation rate calculation is the same as the deflation rate calculation performed in block 212 (FIG. 4), except that mean arterial pressure has been substituted for systolic pressure in accordance with equation (2) above. Block 224 also calculates the new pump-up and hold-in pressures as indicated, and then returns control to block 220 in FIG. 4.

If the error in the preceding measurement cycle did not relate only to the systolic pressure, then control passes from block 222 to block 226. Block 226 determines whether the error related only to the calculation of the systolic and the diastolic pressures. If so, then the deflation rate, pump-up and hold-in parameters are calculated as indicated in block 228. In this circumstance, the deflation rate for the current measurement cycle is set equal to 20 times the pulse rate for the preceding measurement cycle divided by 60 times the PULSE COUNT. This equation is similar to the equation used in block 212 (FIG. 4), except that the value 20 has been substituted for the difference between systolic and diastolic pressures. This conservative assumption is made in an effort to ensure that sufficient pulses will occur between systolic and diastolic pressures in the current measurement cycle to accurately determine blood pressure. Block 228 also calculates the new pump-up and hold-in values as indicated, and then returns control to block 220 in FIG. 4.

All errors, other than those tested for in blocks 222 and 226, will cause the new deflation rate, pump-up and hold-in parameters to be calculated as indicated in block 230. Such "other errors" include an error in the determination of pulse rate. Block 230 determines the deflation rate for the current measurement cycle based upon the deflation rate for the preceding measurement cycle, based upon the following table:

| Preceding Deflation Rate | Current Deflation Rate |
| --- | --- |
| 9 | 5 |
| 8 | 4 |
| 7 | 4 |
| 6 | 3 |
| 5 | 3 |
| 4 | 3 |
| 3 | 2 |
| 2 | 2 | where the above values are expressed in mm/second. Block 230 also calculates the new pump-up and hold-in pressures as indicated from the corresponding values used in the preceding measurement cycle, and then returns control to block 220 in FIG. 4.

While the preferred embodiments of the invention have been illustrated and described, it should be understood that variations will be apparent to those skilled in the art. For example, the deflation rate parameter could be established by means of discrete circuit components rather than by means of a programmed system processor as in the illustrated embodiment. The deflation rate could also be established by averaging or by other techniques that make use of measurements made over two or more prior measurement cycles. Accordingly, the invention is not to be limited to the specific embodiments illustrated and described, and the true scope and spirit of the invention are to be determined by reference to the following claims.

The embodiments of the invention in which an exclusive property or privilege is claimed are defined as follows:

1. A blood pressure measuring device, comprising:
   (a) an inflatable cuff adapted for applying pressure to a patient adjacent a blood vessel;
   (b) cuff inflation and deflation means;
   (c) sensor means for providing sensor signals during cuff deflation corresponding to the cuff pressure and to the blood flow surges in the blood vessel; and
   (d) process control means, the process control means further comprising:
      (i) means for controlling the cuff inflation and deflation means so as to cause inflation of the cuff to a first pressure and subsequent deflation of the cuff from the first pressure to a lower second pressure at a preestablished deflation rate, the inflation and subsequent deflation of the cuff comprising a measurement cycle;
      (ii) calculation means for processing the sensor signals provided during a given measurement cycle and for determining at least one blood pressure value indicative of the patient's blood pressure for that measurement cycle and a pulse rate value indicative of the patient's pulse rate for that measurement cycle; and
      (iii) parameter setting means for establishing the deflation rate for a given measurement cycle based upon the blood pressure value determined during at least one previous measurement cycle and the pulse rate value determined during at least one prior measurement cycle.

2. The device of claim 1, wherein the parameter setting means is operative to establish the deflation rate such that if the patient's blood pressure remains constant between the given measurement cycle and at least the previous measurement cycle, a predetermined number of blood flow surges will occur during the time in the given measurement cycle that the cuff is deflated from the patient's systolic pressure to the patient's diastolic pressure.

3. The device of claim 2, wherein the predetermined number of blood flow surges is in the range of 10 to 12.

4. The device of claim 2, wherein the predetermined number of blood flow surges is 11.

5. The device of claim 1, wherein the calculation means determines values related to the patient's systolic pressure and diastolic pressure for each measurement cycle, and wherein the parameter setting means is operative to establish the deflation rate based upon the systolic pressure, diastolic pressure and pulse rate values for the preceding measurement cycle.

6. The device of claim 5, wherein the means for controlling the cuff inflation and deflation means is operative to cause the cuff to deflate at an approximately linear, preestablished deflation rate.

7. The device of claim 6, wherein the parameter setting means is operative to establish the deflation rate based upon the product of the pulse rate multiplied by the difference between the systolic and diastolic pressures.

8. The device of claim 6, wherein the calculation means determines a value related to the patient's mean arterial pressure for each measurement cycle, and wherein the parameter setting means is operative whenever the mean arterial pressure, diastolic pressure and pulse rate could be determined for the preceding measurement cycle but the systolic pressure could not be determined for the preceding measurement cycle, to establish the deflation rate by determining a value related to the product of the pulse rate multiplied by the difference between the mean arterial pressure and the diastolic pressure for the preceding measurement cycle.

9. The device of claim 6, wherein the parameter setting means is operative, whenever the pulse rate could be determined for the preceding measurement cycle but neither the systolic nor diastolic pressure could be determined for the preceding measurement cycle, to establish the deflation rate by determining a value linearly related to the pulse rate.

10. The device of claim 6, wherein the parameter setting means is operative, whenever the pulse rate could not be determined for the preceding measurement cycle, to establish the deflation rate based upon the deflation rate for the preceding measurement cycle.

* * * * *